US006551317B2

(12) United States Patent
Berish et al.

(10) Patent No.: US 6,551,317 B2
(45) Date of Patent: Apr. 22, 2003

(54) METHOD AND APPARATUS FOR FACILITATING THE HEALING OF BONE FRACTURES

(75) Inventors: Daniel A. Berish, Montville, NJ (US); Henry J. McVicker, Naples, FL (US); Glenn W. Johnson, III, Mendham, NJ (US); Anthony Victor Seaber, Hillsborough, NC (US); Christian Fink, Ebensee (AT)

(73) Assignee: Aircast, Inc., Summit, NJ (US)

( * ) Notice: Subject to any disclaimer, the term of this patent is extended or adjusted under 35 U.S.C. 154(b) by 0 days.

(21) Appl. No.: 09/876,345

(22) Filed: Jun. 7, 2001

(65) Prior Publication Data

US 2002/0035375 A1 Mar. 21, 2002

Related U.S. Application Data

(60) Provisional application No. 60/210,328, filed on Jun. 8, 2000.

(51) Int. Cl.$^7$ ................................................ A61B 17/56
(52) U.S. Cl. ............................. 606/58; 606/57; 606/59
(58) Field of Search .............................. 606/53, 54, 57, 606/58, 59, 102, 241; 601/150, 152

(56) References Cited

U.S. PATENT DOCUMENTS

| 4,502,473 A | * | 3/1985 | Harris et al. |
| 4,570,625 A | * | 2/1986 | Harris et al. |
| 5,496,262 A | | 3/1996 | Johnson, Jr. et al. |
| 5,584,798 A | | 12/1996 | Fox |
| 5,588,955 A | * | 12/1996 | Johnson, Jr. et al. |
| 5,919,192 A | * | 7/1999 | Shouts |
| 6,022,349 A | * | 2/2000 | McLeod et al. |
| 6,039,737 A | * | 3/2000 | Dyer |

OTHER PUBLICATIONS

"A New Concept in Fracture Immobilization: The Application of a Pressurized Brace", P.A. Dale, et al., Clinical Orthopaedics and Related Research, No. 295, pp. 264–269, 1993.
"Venous Pressure and Bone Formulation", Kelly et al., Microvascular Research, 39, pp. 364–375, 1990.
"Investigation of the Role of Venous Pressure in Bone Changes During Prolonged Weightlessness", NcCarthy, Journal of Gravitational Physiology, vol. 3(2), 1996.
"Acceleration of Fracture Healing Distal to a Venous Tourniquet", R.L. Kruse, et al., J.Bone and Joint Surgery, vol. 56–A, No. 4, Jun. 1974.

* cited by examiner

Primary Examiner—Pedro Philogene
(74) Attorney, Agent, or Firm—Jones Day

(57) ABSTRACT

A method and apparatus are disclosed for treating bone fractures by the application of intermittent pneumatic compression. The period of compression is sufficient to induce venous stasis at the fracture site. The period of recovery can be about half the period of compression. The applied pressure can be 50% or less of the baseline pressure.

28 Claims, 5 Drawing Sheets

METHOD AND APPARATUS FOR FACILITATING THE HEALING OF BONE FRACTURES

STATEMENT OF RELATED APPLICATION

This application claims the benefit under 35 U.S.C. 119(e) of copending provisional application Ser. No. 60/210,328, filed Jun. 8, 2000.

FIELD OF THE INVENTION

This invention relates to a method of facilitating the healing of fractured bones. More particularly this invention relates to a method for facilitating the healing of a fractured bone by the application of intermittent pneumatic compression (IPC).

BACKGROUND OF THE INVENTION

Intermittent pneumatic compression is the technique of cyclically compressing a limb with air pressure so as to enhance the circulation of blood. In such prior art systems, pressure is applied from a source of compressed air by a control mechanism to provide a pulse of pressure that intermittently inflates a cuff enveloping all or part of an arm or leg. The rapid inflation of the cuff serves to rapidly force blood out of the veins. The pressure in the cuff is then released, allowing the veins to refill. Parameters that can be controlled include the rate of pressurization, the pressure achieved, the time period of the compression, the rate of depressurization, the time period between pulses, and the total duration of the application of intermittent pneumatic compression. As disclosed in U.S. Pat. No. 5,496,262, assigned to the common assignee and incorporated herein by reference, IPC can also be applied by means of cuffs having more than one chamber, the chambers being disposed at relatively distal and proximal locations along the limb. Additional parameters that can be controlled with multiple-chambered cuffs include the level of pressure that can be provided to each chamber (i.e., graduated compression), and the timing of the application of pressure to each chamber (i.e., sequential compression).

IPC as practiced in the prior art provides enhanced circulation of blood, which is known to be of therapeutic benefit for a variety of circulatory disorders. For example, the use of IPC is known in the prevention and treatment of edema. IPC is also known as a means for reducing the risk of deep vein thrombosis (DVT). U.S. Pat. No. 5,588,955, also assigned to the common assignee and incorporated herein by reference, discloses a method and apparatus for applying graduated and/or sequential IPC to a limb to prevent DVT. Applicant's assignee also manufactures and sells devices under the trademarks VENAFLOW® and ARTERIALFLOW® which are used to apply IPC to a patient in need of such therapy.

As disclosed in the aforementioned U.S. Pat. No. 5,496,262 and U.S. Pat. No. 5,588,955, in IPC as used in the prior art the period of compression is typically short, about ten seconds, and rapidly emptied by the short pulse of compression. The optimal amount of compression used in prior art devices is in the range of 35–45 mmHg. Further, it is known that the velocity of venous flow during the period of compression is proportional to the rate of pressurization. For example, a pulse that reaches maximum pressure in six seconds will have a much greater effect on venous velocity than a pulse that reaches the same maximum pressure in 30 seconds.

It has been suggested in the medical literature that application of prolonged compression may promote healing of a bone fracture. In "Acceleration of Fracture Healing Distal to a Venous Tourniquet," R. L. Kruse, et al., *J. Bone and Joint Surgery*, vol. 56-A, No. 4, June 1974, it was reported that the continuous use of a hand-wrapped venous tourniquet was shown to increase new bone formation at fracture sites and in defects in bone, and to accelerate fracture healing. In "A New Concept in Fracture Immobilization: The Application of a Pressurized Brace," P. A. Dale, et al., *Clinical Orthopaedics and Related Research*, No. 295, pp. 264–269, 1993, it was found that continuous use of a static pressurized brace made by Aircast, Inc. of Summit, N.J., the assignee of the instant application, yielded a stronger healed fracture than did a traditional cast. The pressurized brace in that study provided an average skin-to-brace pressure of about 29 mmHg; applied constantly for at least six weeks.

In "Venous Pressure and Bone Formation," Kelly, et al., *Microvascular Research*, 39, 364–375 (1990), a specially designed venous tourniquet from Aircast was applied continuously for several weeks to broken bones in animal limbs. Those limbs in which venous pressure was increased with the continuous application of the venous tourniquet compression experienced an increase in new bone formation.

In "Investigation of the Role of Venous Pressure in Bone Changes During Prolonged Weightlessness," McCarthy, *Journal of Gravitational Physiology*, Vol. 3 (2), (1996), a venous tourniquet system (VTS) comprising an intermittent pneumatic compression system in which a peak pressure of 60 mmHg is applied in a cycle of 30 seconds on/30 seconds off for a total time of one hour per day in conditions of weightlessness was studied to determine if the VTS would prevent bone loss normally associated with prolonged weightlessness. Conclusive data from this study has not yet been published.

Prior attempts at using continuously applied venous tourniquet compression for the promotion of fracture healing have not been fully successful because of the pain and discomfort to the skin of the patient resulting from the continuous application of the tourniquet. Continuously applied tourniquet compression could also create other undesirable side effects such as transient neuropathy, edema, and soft tissue damage related to ischemia.

Thus one object of the invention to provide a method for facilitating the healing of bone fractures yet which minimizes undesirable side effects including skin discomfort and related disorders that can arise from continuously applied tourniquet compression.

It is another object of the invention to provide an apparatus for facilitating the healing of bone fractures yet which minimizes undesirable side effects including skin discomfort and related disorders that can arise from continuously applied tourniquet compression.

SUMMARY OF THE INVENTION

In accordance with the invention, a method for facilitating the healing of bone fractures comprises applying intermittent pneumatic compression at or proximal to the site of a bone fracture at a predetermined pressurization and time cycle. The invention also includes an apparatus for carrying out the method, the apparatus comprising an inflatable cuff capable of being applied to a site at or proximal to the bone fracture, and a pump in fluid communication with the inflatable cuff, the pump being controlled by a timer to pressurize the cuff at a predetermined pressurization rate and at a predetermined time cycle. It has been found that by selection of appropriate pressurization and time cycles, the IPC device can be used to create tourniquet-like compression for periods of time sufficient to promote healing of bone fractures, while allowing recovery periods sufficient to alleviate some of the adverse effects that can occur with continuously applied tourniquet compression.

DETAILED DESCRIPTION OF THE INVENTION

Figure 1:
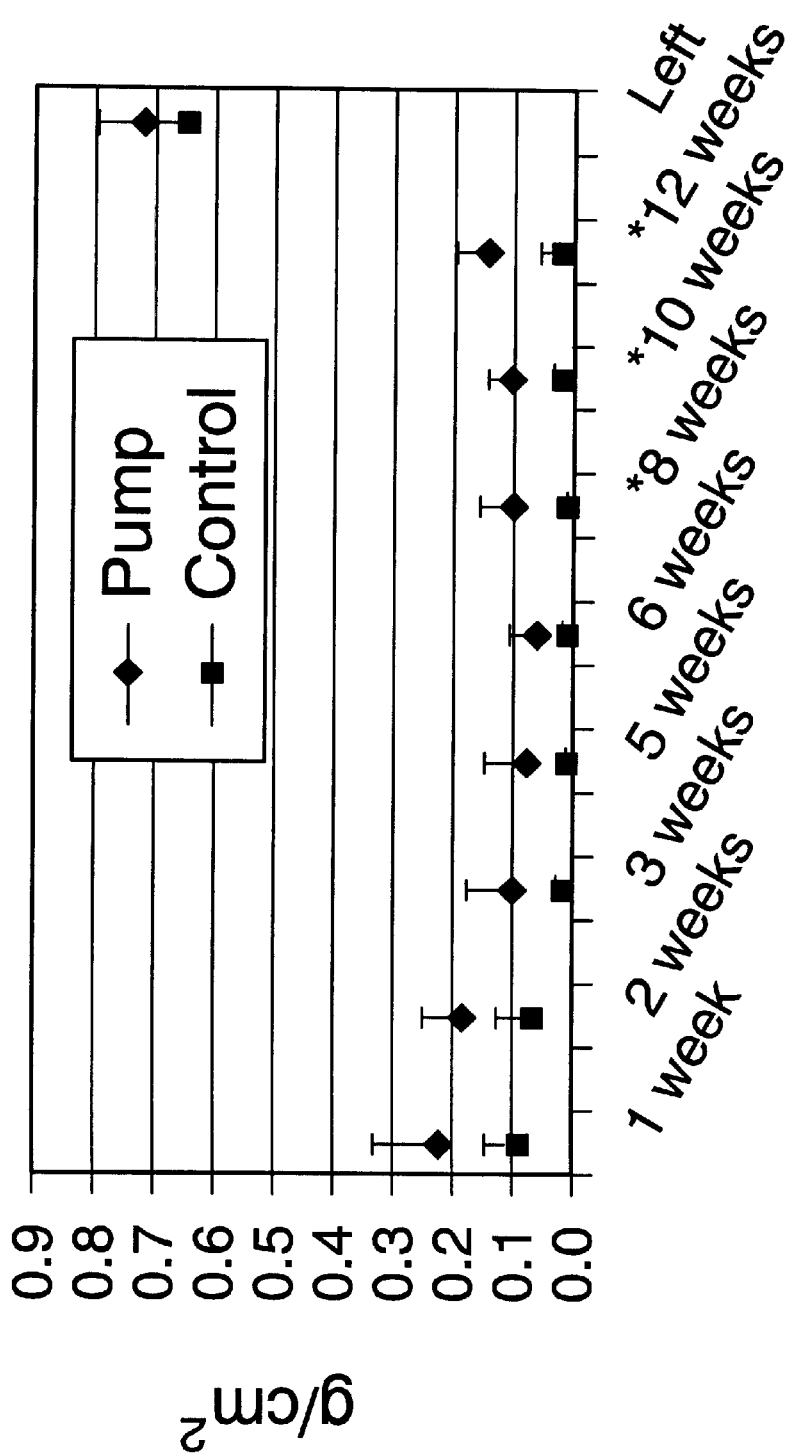
FIG. 1 is a graph comparing the bone mineral density at the fracture gap in an experimental group of animals treated with the method and apparatus of the instant invention compared with a control group.

The instant invention comprises a method and apparatus for facilitating the healing of a bone fracture by applying intermittent pneumatic compression to a region proximal to the bone fracture. In one embodiment, the apparatus can be similar to that illustrated in FIG. 1 of the aforementioned U.S. Pat. No. 5,588,955, although the settings for the periods of compression and recovery will be very different, as explained below. In the currently known preferred embodiment, an inflatable cuff means can be contained within a brace, a garment, or a cast, and applied to partially or completely encircle the region at or proximal to the fracture. The inflatable cuff means is connected by means of a small tube to an air pump which is connected to control means, such as a timer, and a power source such as a battery pack. The maximum pressure of the inflatable cuff means can be regulated by a pressure release valve.

During the prescribed time cycle the pump is activated and the cuff or bladder is inflated to the desired pressure. Unlike prior art IPC systems which served to increase venous velocity and enhance circulation, the method and apparatus of the instant invention operate to partially occlude the venous system to provide venous stasis in the region of the bone fracture.

Although the mechanism by which the instant invention promotes the healing of bone fractures is not known with certainty at this time, it is currently believed that the method and apparatus provide a transmural pressure gradient which promotes interstitial fluid flow from the intramedullary cavity outward through the bone. That is, the pressure gradient induced by the method and apparatus of the invention causes fluid to flow from areas of compression to areas of tension, thus positively influencing bone remodeling in the area of the fracture. In particular, it is believed that the increased compression for a pre-determined time period increases osmotic pressure to allow the diffusion of blood, and therefore nutrients, to those cells at the site of the injury that require those nutrients for bone formation.

In contrast to prior art IPC systems which use a rapid pulse of pressurization that is maintained for about 10 seconds, in the method and apparatus of the instant invention the compression can be maintained for as long as several minutes. Also, while in the prior art IPC systems the period of recovery can be substantially longer than the period of compression, in the method and apparatus of the instant invention the period of recovery can be substantially shorter than the period of compression. In the method of the instant invention, as presently understood, the period of compression can be on the order of about 2–15 minutes, more preferably about 4–10 minutes, and in the present preferred embodiment about 5 minutes. The period of recovery can be on the order of about 0.5–4 minutes, more preferably about 2–3 minutes, and in the present preferred embodiment about 2.5 minutes. Alternatively, the period of recovery can be about 50% or less of the period of compression.

The time period and level of compression will be sufficient to cause venous stasis. Typically, the level of such compression will be at least about 30–75% of the baseline compression (i.e., the resting venous pressure of the individual) at the site of the fracture, and more preferably at least about 50% of the baseline compression. The level of baseline compression will depend on the location of the bone fracture. For example, the proximal portion of a limb will have a greater baseline compression than a distal portion.

It is believed that the instant invention has its greatest applicability to bone fractures in the limbs, and those bone fractures that can be treated with biophysical methods for augmenting normal biological processes. Such prior art biophysical methods include electrical stimulation, which can include constant direct current stimulation by implanted electrodes, time varying inductive coupling by a magnetic field, and capacitative coupling, or low intensity pulsed ultrasound techniques. It is further believed that the method and apparatus of the instant invention will find particular utility in those cases of bone fracture that are particularly difficult to heal including delayed union bone fractures, such that the instant invention will promote healing of these fractures in less time than previously experienced. It will be within the scope of the invention to optimize the duration, frequency, pressure and treatment time to produce the maximum duration of increased venous pressure significantly above baseline values to induce venous stasis while avoiding the undesirable side effects of the prior art tourniquet systems, including skin discomfort and swelling.

An embodiment of the inventive method and apparatus will be described in relation to certain animal studies demonstrating the efficacy of the invention. However, the invention is not intended to be limited to the particular parameters, including pressures and time cycles, used in these studies. In one preliminary study, six dogs were treated surgically to create a delayed union by making a 3 mm wide defect completely across the radius. The ulna was left intact such that the animals remained ambulatory. This model was chosen because it best represents delayed healing in a non-weight bearing bone. Three of the dogs were used as controls and were not treated with the method and apparatus of the invention. For each of the other three dogs, an inflatable circumferential cuff was applied to the animal proximal to the surgical defect. A pressure of 45 mmHg was applied for a cycle of five minutes on, two and one-half minutes off, for 12 hours a day. Treatment was begun eight days after the surgery and continued for a period of six weeks. It was found that the animals with the defects and treated with the method and apparatus of the instant invention exhibited more periosteal bone growth, more endosteal bone growth, and greater progression of the healing process than the untreated animals.

Figure 2:
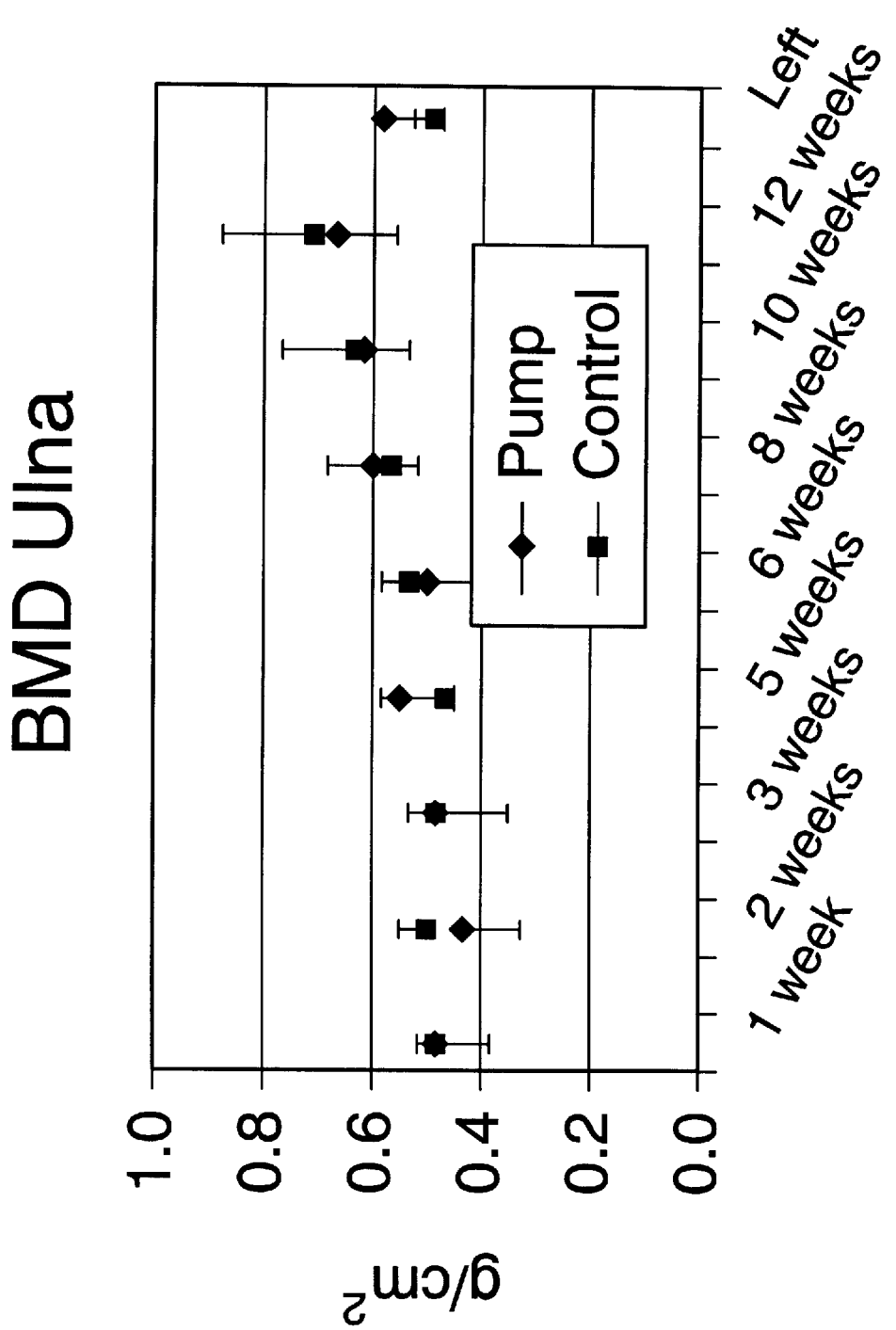
FIG. 2 is a graph comparing the bone mineral density in an unbroken bone in an experimental group of animals treated with the method and apparatus of the instant invention compared with a control group.

In a follow-up study, the same surgery was performed on twelve dogs. Six of the dogs were treated with the apparatus described above, with a pressure of 46 mmHg being applied for a period of five minutes on, two and one half minutes off, 13 hours per day for eight weeks. The other six dogs were a control group not treated with inventive method and apparatus. As illustrated in the graph of FIG. 1, after eight weeks, the bone mineral density at the fracture gap was statistically significantly greater for the treated group than for the control group. As illustrated in the graph of FIG. 2, there was no statistically significant difference in the bone mineral density of the ulna, which is the bone adjacent to the radius in which the fracture gap was surgically introduced, and which ulna therefore was also subjected to the same pressurization cycle.

Figure 3A:
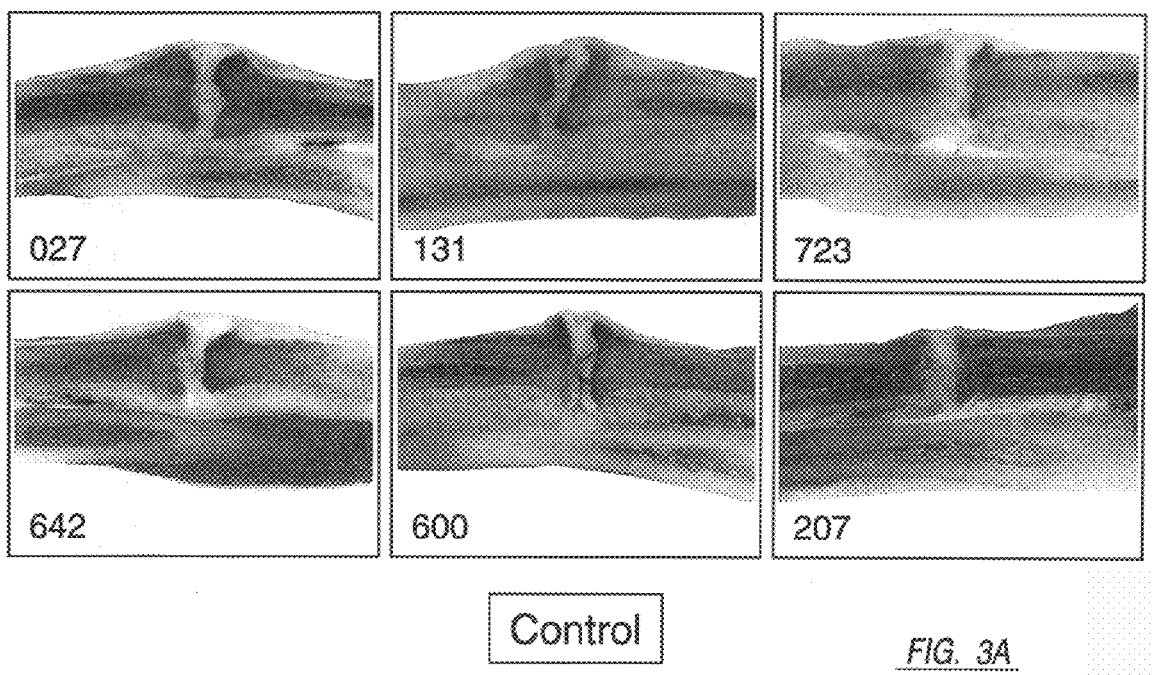
FIG. 3A is a set of photographs of the radius and ulna of a control group of animals, in which an axial cut has been made along both the radius and the ulna.
Figure 3B:
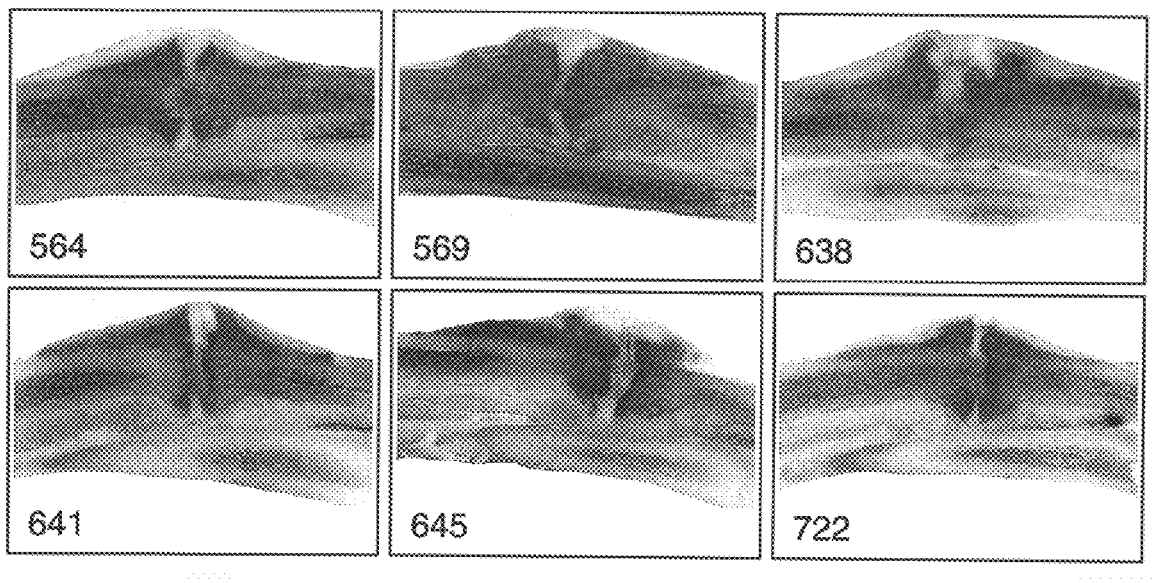
FIG. 3B is a set of photographs of the radius and ulna of an experimental group of animals treated with the method and apparatus of the instant invention, in which an axial cut has been made along both the radius and the ulna.
Figure 4:
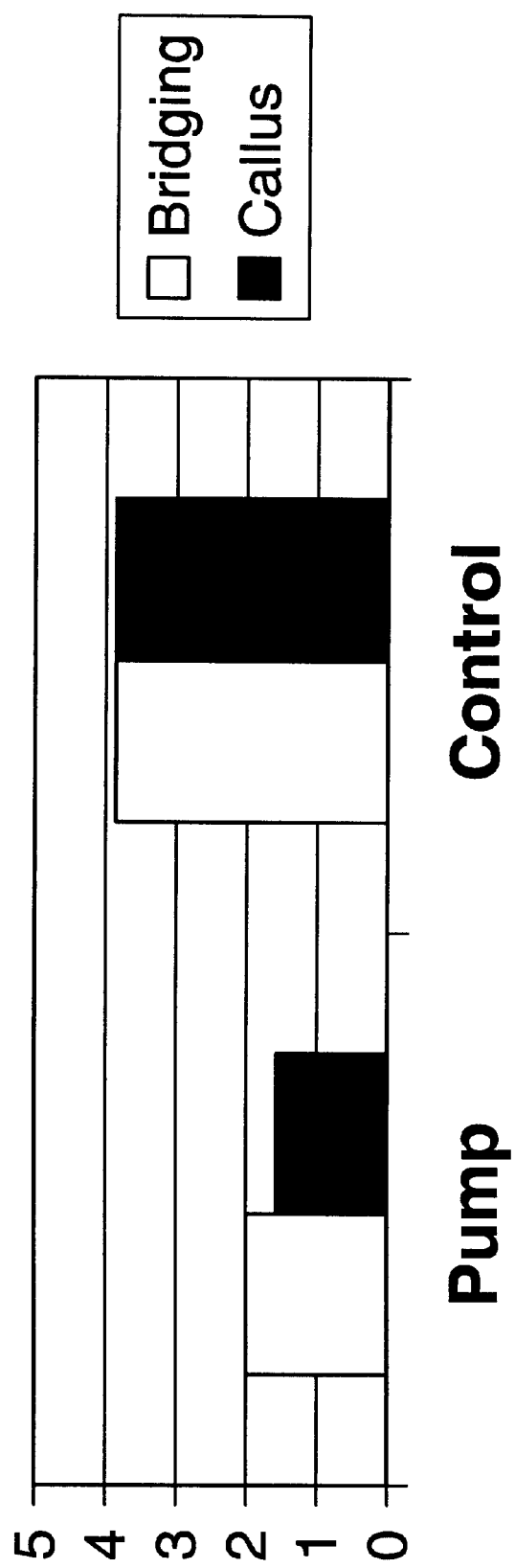
FIG. 4 is a graph showing subjective ratings by radiologists of the extent of healing in a control group of animals compared with a group of animals treated with the method and apparatus of the instant invention.

FIGS. 3A and 3B are photographs of the control group and the treated group, respectively, about twelve weeks after the surgical introduction of the bone defect in the radius, in which an axial cut was made along both the radius, shown in the top part of each photo, and the ulna, shown in the bottom part of each photo. It may be seen that in the control group, a substantial amount of callus remains across the fracture gap. This callus indicates that the healing process is still in its early stages. In the group treated with the instant invention it may be seen that bridging has occurred from one end of the bone to the other, with callus developing beneficially surrounding the outer area of the bone. This indicates that the healing process has progressed more than in the control group.

The extent of bridging and callus as between the two groups was subjectively rated by trained radiologists who were "blinded" to the underlying data, i.e. the radiologists did not know which of the animals were of the treated group and which were of the control group. The ratings were based on a scale of 0–5 in which 0 indicates complete healing and 5 indicates no healing. The ratings indicate that the group treated with the method and apparatus of the invention fared significantly better in terms of both bridging and beneficial callus than the control group.

What is claimed is:

1. A method of treating a bone fracture, the method comprising the step of applying intermittent low pressure pneumatic compression directed radially inwardly at or proximal to the site of the bone fracture at a pre-determined pressure and for pre-determined periods of compression and recovery, said period of compression being sufficient to cause venous stasis in the region of the fracture and said period of recovery being sufficient to restore venous circulation.

2. The method of claim 1 wherein said pre-determined period of compression is in the range of about 2–15 minutes.

3. The method of claim 2 wherein said pre-determined period of recovery is in the range of about 0.5–4 minutes.

4. The method of claim 1 wherein said pre-determined period of compression is in the range of about 4–10 minutes.

5. The method of claim 4 wherein said pre-determined period of recovery is in the range of about 2–3 minutes.

6. The method of claim 1 wherein said pre-determined period of compression is about 5 minutes.

7. The method of claim 6 wherein said pre-determined period of recovery is about 2.5 minutes.

8. The method of claim 1 where said predetermined period of recovery is about 50% of said period of compression.

9. The method of claim 1 wherein said pre-determined pressure is about 50% of the baseline pressure, or less.

10. The method of claim 1 wherein said pre-determined pressure is about 50 mmHg or less.

11. A method of treating a bone fracture, the method comprising alternately (a) applying compression at or proximal to the site of the bone fracture, at sufficient pressure and for a pre-determined period of time to cause venous stasis, and (b) reducing the applied pressure for a pre-determined period of time to relieve venous stasis.

12. The method of claim 11 wherein said predetermined period of compression is in the range of about 2–15 minutes.

13. The method of claim 12 wherein said pre-determined period of recovery is in the range of about 0.5–4 minutes.

14. The method of claim 11 wherein said pre-determined period of compression is in the range of about 4–10 minutes.

15. The method of claim 14 wherein said pre-determined period of recovery is in the range of about 2–3 minutes.

16. The method of claim 11 wherein said pre-determined period of compression is about 5 minutes.

17. The method of claim 16 wherein said pre-determined period of recovery is about 2.5 minutes.

18. The method of claim 1 where said predetermined period of recovery is about 50% of said period of compression.

19. The method of claim 1 wherein said predetermined pressure is about 50% of the baseline pressure, or less.

20. The method of claim 1 wherein said pre-determined pressure is about 50 mmHg or less.

21. A method of treating a bone fracture, the method comprising cyclically applying compression directed radially inwardly at or proximal to the site of the bone fracture, at a pressure about 50% or less above the baseline pressure, for a pre-determined period of compression, and reducing said applied compression for a pre-determined period of recovery.

22. The method of claim 21 wherein said pre-determined period of compression is in the range of about 2–15 minutes.

23. The method of claim 22 wherein said pre-determined period of recovery is in the range of about 0.5–4 minutes.

24. The method of claim 21 wherein said pre-determined period of compression is in the range of about 4–10 minutes.

25. The method of claim 24 wherein said pre-determined period of recovery is in the range of about 2–3 minutes.

26. The method of claim 21 wherein said pre-determined period of compression is about 5 minutes.

27. The method of claim 26 wherein said pre-determined period of recovery is about 2.5 minutes.

28. The method of claim 21 where said pre-determined period of recovery is about 50% of said period of compression.

* * * * *